United States Patent [19]

Miller et al.

[11] Patent Number: 5,077,447

[45] Date of Patent: Dec. 31, 1991

[54] PROCESS FOR MAKING OLEFINS

[75] Inventors: Joseph A. Miller; Jeffrey A. Nelson; Mike Byrne, all of Santa Rosa, Calif.

[73] Assignee: Henkel Research Corporation, Santa Rosa, Calif.

[21] Appl. No.: 589,741

[22] Filed: Sep. 28, 1990

[51] Int. Cl.$^5$ .............................................. C07C 1/00
[52] U.S. Cl. ...................................................... 585/638
[58] Field of Search .......................................... 585/638

[56] References Cited

U.S. PATENT DOCUMENTS

| | | | |
|---|---|---|---|
| 2,601,536 | 6/1952 | La Zerte | 260/653 |
| 2,926,203 | 2/1960 | Brooks | 260/653.3 |
| 3,109,040 | 10/1963 | Lee | 260/681 |
| 3,530,198 | 9/1970 | Fenton | 260/682 |
| 3,531,387 | 9/1970 | Cyba et al. | 204/72 |
| 3,625,996 | 12/1971 | Fenton | 260/486 |
| 4,178,317 | 12/1979 | Horn et al. | 585/357 |
| 4,554,397 | 11/1985 | Stern et al. | 585/638 |

FOREIGN PATENT DOCUMENTS 75-14603 2/1975 Japan .

OTHER PUBLICATIONS

Journal of the American Oil Chemists Society, 53, 737 (1976), Foglia, Barr.
Journal of Organic Chemistry, 48(20), 3575-3577, (1983), Fristad, Fry, Klang.
R. F. Heck, Palladium Reagents . . . Syntheses, Academic Press, NY, N.Y. 1985, pp. 1-7, p. 18.
Organotransition Metal Chemistry . . . Synthesis, Pergamon Press, NY, N.Y., 1985, 13-17.
Perry's Chemical Engineer's Handbook, 6th Ed., pp. 11-33 & 11-34.

*Primary Examiner*—Curtis R. Davis
*Attorney, Agent, or Firm*—Ernest G. Szoke; Wayne C. Jaeschke; John E. Drach

[57] ABSTRACT

Carboxylic acids are converted in high yields to olefins or high purity α-olefins by contacting a mixture of carboxylic acid and a carboxylic acid anhydride in the presence of a Group VIII metal or copper-containing catalyst at a temperature of from about 100° C. to about 300° C.

63 Claims, No Drawings

PROCESS FOR MAKING OLEFINS

1. FIELD OF THE INVENTION

This invention relates to a process for making olefins in high yield by reaction of a mixture of carboxylic acids and anhydrides in the presence of a catalyst. The invention further relates to a process which is highly specific for making α-olefins.

2. DESCRIPTION OF THE RELATED ART

α-Olefins are used in the manufacture of a variety of commercially important materials. For example, higher alcohols made by hydroformylation (Oxo Process) of $C_6$–$C_{18}$ α-olefins are used primarily as plasticizers. α-Olefin sulfonates (AOS) are used in detergent formulations and are made by reaction of $C_{12}$–$C_{18}$ α-olefins with $SO_3$ followed by neutralization and hydrolysis with sodium hydroxide. Ethoxylated and sulfated detergent range alcohols which are the hydroformylation products of $C_{12}$–$C_{18}$ α-olefins are also used as detergents. Certain types of synthetic lubricants are made by hydrogenation of α-olefin oligomers.

Normally α-olefins are made by wax cracking or oligomerization of ethylene with Ziegler catalysts. However, there has been an increasing urgency to find a source of α-olefins from renewable, non-petroleum resources in recent years. Most of the work in this area has been concentrated on producing αolefins from fatty acids or their derivatives. The initial reports were concerned with the production of fluorinated 1-olefins by pyrolysis of carboxylic acids. For example, U.S. Pat. No. 2,601,536 teaches that perfluoro-1-olefins can be produced by heating alkali metal salts of perfluorinated carboxylic acids to a temperature in the range of from 200° C. to 300° C. Similarly, U.S. Pat. No. 2,926,203 teaches that perfluoro-1-olefins can be produced by heating perfluorinated carboxylic acids having 3 to 13 carbon atoms to a temperature in the range of from 400° C. to 650° C. The selective production of 1-olefins from the pyrolysis of aliphatic carboxylic acids was first reported in U.S. Pat. No. 3,109,040. This patent teaches that stearic anhydride can be converted to 98% pure 1-heptadecene in 46% yield and stearic acid in acetic anhydride can be converted to 98% pure 1-heptadecene in 66% yield by heating the vapors in both instances to a temperature in the range of from 350° C. to 700° C. The Journal of the American Oil Chemists Society, 53, 737 (1976) teaches the catalytic decarbonylation of stearic acid by rhodium and palladium catalysts at about 280° C. produces an isomeric mixture of heptadecenes. The composition of the mixture depends upon the type of rhodium or palladium catalyst. The product obtained by this route was never comprised solely of the 1-olefin. A mixture of 1-, 2-, and 3-olefins was always obtained in all cases. U.S. Pat. No. 3,530,198 teaches that a mixture of positional isomers of olefins are obtained by contacting carboxylic acids, esters, anhydrides, or acid halides with a complex catalyst comprising a Group VIII noble metal and a biphyllic ligand such as an organic phosphine, arsine, or stibine at a temperature of from about 100° C. to about 300° C. at various pressures and with substantial removal of the olefin as it is formed. U.S. Pat. No. 3,530,198 does not teach a combination of carboxylic acid and carboxylic acid anhydride in the reaction mixture. Although the patent teaches that carboxylic acid anhydrides can be used as starting materials in the process to produce olefins, it does not contemplate their use in combination with carboxylic acids since it teaches that the carboxylic acid anhydrides useful in the claimed process must have at least 3 carbon atoms. The process according to the present invention specifically points out that while any carboxylic acid can be used, acetic anhydride, which contains 2 carbon atoms, is especially preferred. There is also no teaching in U.S. Pat. No. 3,530,198 of α-olefin selectivity greater than 75% or high catalyst turnover numbers. U.S. Pat. No. 3,531,387 teaches a process for the highly specific preparation of α-olefins by electrolysis of an aqueous methanol solution of a paraffinic-type carboxylic acid in the presence of a bivalent copper salt catalyst. U.S. Pat. No. 3,625,996 teaches the catalytic preparation of olefinic acids and esters from dicarboxylic acids using the same methodology as taught in U.S. Pat. No. 3,530,198. JP 50047904 and Japanese Kokai 75 14,603 teach a process for the selective synthesis of olefins over ketones by heating a carboxylic acid or ester over a silico, wolframic acid, tungstomolybdophosphoric acid and phosphorus wolframic acid catalyst at a temperature of about 250° C. U.S. Pat. No. 4,178,317 teaches that aliphatic and cycloaliphatic olefins can be made by contacting an aliphatic and cycloaliphatic carboxylic acid in the gas phase with a catalyst in which the active material is comprised of a combination of a compound selected from boron trioxide, boric acid, boron nitride and a compound selected from aluminum oxide, silicon dioxide, titanium dioxide, and zirconium dioxide. U.S. Pat. No. 4,554,397 teaches the manufacture of a linear olefin by contacting a fatty acid or ester with a catalyst comprised of nickel and at least one of elemental tin, germanium, and lead at a temperature of from 200° C. to 400° C. The Journal of Organic Chemistry, 48(20). 3575–3577, (1983) teaches the preparation of alkenes by reacting a carboxylic acid and Ag(II) ion in refluxing acetonitrile.

None of the prior art processes teaches or suggests a process for making olefins from carboxylic acids in high yield or a process which is at least 90% selective for making αolefins in high yield and a high catalyst turnover number which comprises the combination of the steps of heating a mixture of a carboxylic acid, a carboxylic acid anhydride and a Group VIII metal-containing catalyst or copper-containing catalyst while continuously removing the α-olefin-rich product formed in the reaction.

SUMMARY OF THE INVENTION

One aspect of the present invention provides a process for making olefins in high yield comprising maintaining a reaction mixture comprised of a carboxylic acid wherein said carboxylic acid has at least three carbon atoms and at least one β-hydrogen atom, a carboxylic acid anhydride, and a Group VIII metal-containing catalyst or a copper-containing catalyst at a temperature of from about 100° C. to about 300° C. Another aspect of the invention provides a process which is highly selective for making α-olefins in high yield comprising maintaining a reaction mixture comprised of a carboxylic acid wherein said carboxylic acid has at least three carbon atoms and at least one β-hydrogen atom, a carboxylic acid anhydride with a Group VIII metal-containing catalyst or a copper-containing catalyst at a temperature of from about 100° C. to about 300° C. to form an olefin product comprised of at least 90% by weight of an α-olefin while continuously removing said olefin product from said reaction mixture.

Each aspect according to the invention provides a process which is particularly useful for making olefins in commercial quantities under very favorable economic conditions because of the high overall yield of olefin product and the very low catalyst usage per mole of olefin produced.

anhydride based on decanoic acid produces an over thirty-fold increase in the catalyst TON and an over five-fold increase in α-olefin selectivity in a reaction using a palladium-based catalyst.

TABLE 1

$$C_9CO_2H/Ac_2O + ML_n \xrightarrow[255°\ C.]{PPh_3\ (10\ mol\ \%)} C_7CH{=}CH_2$$
(1:1)    (1 mol %)

| | Without Ac$_2$O | | | With Ac$_2$O | | |
|---|---|---|---|---|---|---|
| ML$_n$ | TON | TON/hr | α-selectivity | TON | TON/hr | α-selectivity |
| (Ph$_3$P)$_2$NiCl$_2$ | 24 | 13 | 25 | 50 | 20 | 33 |
| (Ph$_3$P)$_2$PdCl$_2$ | 16 | 60 | 17 | 520 | 800 | 92.5 |
| (Ph$_3$P)$_2$PtCl$_2$ | 27 | 9 | 58 | 130 | 41 | 79.4 |
| (Ph$_3$P)$_2$Rh(CO)Cl | 105 | 7 | 90.2 | 310 | 12 | 94.0 |
| (Ph$_3$P)$_2$Ir(CO)Cl | 270 | 20 | 54 | 1280 | 65 | 91.5 |
| (Ph$_3$P)$_3$CuCl | 0 | — | — | 35 | 7 | 99.5 |

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about". The term α-olefin selectivity as used herein means the ratio expressed as a percent of α-olefin (1-alkene) to the total olefins produced in the reaction. For example, if the decarbonylation of pentanoic acid by the process according to the invention occurs with 98% α-olefin selectivity, 98% of the total olefin is 1-butene and the sum of all of the other possible olefins (such as cis- and trans-2-butene) is a total of 2%. As used herein, the term catalyst turnover number, abbreviated TON, means the number of moles of olefin product produced per mole of catalyst utilized. Also as used herein, the term olefin product means the total of all the olefins formed in the decarbonylation of a carboxylic acid.

In each aspect of the invention, the carboxylic acid can be any carboxylic acid having 3 or more carbon atoms and which has a B-hydrogen atom. A β-hydrogen atom is a hydrogen atom bonded to a β-carbon atom which is carbon atom number three. The preferred carboxylic acids are those which have from about 8 to about 22 carbon atoms such as decanoic acid, myristic acid, stearic acid, palmitic, lauric, and oleic acid. The carboxylic acid can also a dicarboxylic acid having from at least 4 to about 20 carbon atoms between the carboxyl groups such as adipic acid, azelaic acid, sebacic acid, suberic acid, and pimelic acid. The carboxylic acid anhydride can be any carboxylic acid anhydride and does not have to be the anhydride of the carboxylic acid used in the process to make the α-olefin. The preferred anhydrides are acetic anhydride and propionic anhydride with acetic anhydride being the most preferred. The presence of anhydride in the reaction mixture is an essential feature of both aspects of the invention. On the one hand, the presence of the anhydride assures a high catalyst TON and high yield while on the other hand anhydride incorporation assures high α-olefin selectivity, high yield and high catalyst TON. The effect of the presence of acetic anhydride on the α-olefin selectivity and catalyst TON is shown in Table 1 for the reaction of decanoic acid as shown below. For example, the inclusion of an equimolar amount of acetic The molar ratio of carboxylic acid/carboxylic acid anhydride can range from about 1/0.5 to about 1/1.5 with the most preferred ratio being about 1/1. The 1/1 molar ratio of carboxylic acid/carboxylic acid anhydride is about optimum for economic purposes.

When a compound containing both a carboxylic acid and carboxylate ester functionality is used in the processes according to the invention, the carboxylate ester group is not affected. For example, if dodecanedioc acid mono-methyl ester is used in the processes according to the invention methyl 10-undecenoate is the principal olefinic product obtained. In addition, if a mono ester such as methyl dodecanoate (methyl laurate) is used in the processes according to the invention no olefinic product is produced and the methyl dodecanoate is recovered essentially quantitatively.

A Group VIII metal is Fe, Co, Ni, Ru, Rh, Pd, Os, Ir, or Pt. The catalysts which can be used in the processes according to the invention include salts, carbonyl compounds, chelates, or complexes with ligands having trivalent donor groups of the metals in Group VIII or copper which are hereinafter referred to as complex catalysts. Complex catalysts are those with ligands having trivalent donor atoms and are comprised of a Group VIII metal complexed by one or more ligands. These complexes are formed by the reaction of a Group VIII metal compound and a ligand having a trivalent donor atom. Such trivalent donor atoms include phosphorus, nitrogen, arsenic, antimony and bismuth. These types of complexes are well known to those of ordinary skill in the art and most commonly involve phosphorus-type ligands. (see R. F. Heck, Palladium Reagents in Organic Syntheses, Academic Press, N.Y., N.Y., 1985, pages 1-7; S. G. Davies, Organotransition Metal Chemistry Applications to Organic Syntheses, Pergamon Press, N.Y., N.Y., 1985, pages 13-17). Examples of the most common phosphorus-type ligands include phosphines of which the preferred are triphenylphosphine, trimethylphosphine, methyldiphenylphosphine, dimethylphenylphosphine, dicyclohexylphenylphosphine, diphenylenephenylphosphine, tri-p-tolylphosphine, tri-(p-chlorophenyl)phosphine, tris(p-methoxyphenyl)phosphine, bis-(diphenylphosphino)methane, 1,2-bis-(diphenylphosphino)ethane, bis-(dicyclohexylphosphino)ethane, bis-(2-diphenylphosphinoethyl)phenylphosphine, 1,1,1-tris-(diphenylphosphinomethyl)ethane, tris-(2-diphenylphosphinoethyl)phosphine, 1,1,4,7,10,10-hexaphenyl-1,4,7,10-tetraphosphadecane, and 1,1-bis-(diphenylphosphino)ferrocene. The complex catalysts are used in conjunction with a ligand having a trivalent donor atom. The preferred ligand is phosphine or a phosphine derivative such as those listed above. The relative amounts of phosphine and Group VIII metal which can be used in the processes according to the invention are best expressed as a ratio of the number of moles of phosphorus in the phosphine compound to the number of moles of Group VIII metal. The phosphorus/Group VIII metal ratio which can be used in the processes according to the invention falls within the range of from about 1/1 to about 1000/1 moles of phosphorus per mole of Group VIII metal. The preferred range is from about 2/1 to about 100/1.

The preferred catalysts are salts, carbonyl compounds, chelates, or complexes of Ni, Rh, Pd, Ir, Pt, and Cu. The most preferred catalysts are salts, carbonyl compounds, chelates, or complexes of Ir, Rh, and Pd. Particularly preferred catalysts are $RhCl_3$, $PdCl_2$, $PdBr_2$, $IrCl_3$, $Pd(OOCCH_3)_2$, $(RhCl(CO)_2)_2$, $(RhCl(C_2H_2)_2)_2$, $(\phi_3P)_3RhCl$, $(\phi_3P)_2PdCl_2$, $(\phi_3P)_2Rh(CO)Cl$, $(Me_2\phi P)_2Rh(CO)Cl$, and $(\phi_3P)_2Ir(CO)Cl$.

In the aspect of the invention which provides a process for making olefins in high yield, the product produced is a mixture of olefins which comprises any and all of the possible internal olefins as well as the α-olefin that can be formed in the process. For example, the olefin product formed by carrying out the process using pentanoic acid results in a product mixture containing 1-butene and all of the other possible olefins (such as cis- and trans-2-butene) in about at least 94% yield based on the amount of pentanoic acid consumed. The yield is based on the amount of consumed carboxylic acid because some of the carboxylic acid distills out of the reaction mixture as the processes according to the invention are carried out. The amount of consumed carboxylic acid is the amount introduced into the process minus the amount which distills out. In all cases, the processes according to the invention produce reaction products containing very little side product, usually equal to or less than about 1% by weight.

In the aspect of the invention which provides a process which is highly selective for making α-olefins in high yield, the product formed and removed from the reaction mixture as rapidly as possible is the olefin product which typically contains at least 90% by weight of the α-olefin formed from the decarbonylation of the corresponding carboxylic acid. For example, the olefin product formed by carrying out the process using stearic acid contains at least 90% by weight 1-heptadecene and more typically at least 95% by weight 1-heptadecene. The nature of the phosphorus ligand plays a major role in determining the α-olefin selectivity and the catalyst turnover number. Dimethylphenylphosphine is especially effective in producing a high αolefin selectivity and high TON. A preferred catalyst which is particularly effective in achieving high α-olefin selectivity and high TON is $(Me_2\phi P)_2Rh(CO)Cl$. The catalyst is employed in the processes according to the invention in the range of from about $10^{-6}$ mole % to about 10.0 mole % based on the number of moles of carboxylic acid introduced into the reactor. The amount of carboxylic acid introduced into the reactor will vary according to the type of process utilized. In the aspect of the invention which provides a process which is highly selective for making α-olefins in high yield, the amount of carboxylic acid introduced into the reactor refers to the amount of carboxylic acid in the feed. In the aspect of the invention which provides a process for making olefins in high yield, the amount of carboxylic acid introduced into the reactor refers to the amount of carboxylic acid placed into the reactor at the beginning of the reaction. The amount of catalyst also varies according to the type of metal present in the catalyst. In the case of rhodium-containing catalysts, for maximum α-olefin selectivity the amount of catalyst varies from about 0.1 mole % to about 1.0 mole % while palladium-containing catalysts are employed in the range of from about $10^{-2}$ to about $10^{-3}$ mole %.

The catalyst lifetime and α-olefin selectivity are affected by an excess of phosphine ligand when palladium and rhodium catalysts are used. In the case of rhodium catalysts, the presence of excess phosphine also strongly impedes the rate of conversion of carboxylic acid to α-olefin. Therefore, optimum catalyst lifetime and α-olefin selectivity are best achieved by adding a volatile phosphine such as dimethylphenylphosphine continuously by itself in the case of the batch process or with the carboxylic acid-anhydride feed in the case of the continuous process. In processes employing palladium catalysts, the excess phosphine is simply added to the reaction all at once.

In the aspect of the invention which provides a process which is highly selective for making α-olefins in high yield, it is essential that the olefin product be removed continuously from the reaction mixture as rapidly as it is formed. The most efficient method of removing the olefin product is by distillation. Since the reaction temperature must be in the range of from about 100° C. to about 300° C., the process may be carried out at any pressure necessary for the facile removal of the olefin product formed. For example, if the olefin product contains an α-olefin which has a relatively high boiling point, the process is carried out at a total pressure less than one atmosphere. On the other hand, if the olefin product contains an α-olefin which has a relatively low boiling point, the process is carried out at a total pressure greater than one atmosphere in order to reach the temperature at which the carboxylic acid will decarbonylate. The pressure at which to carry out the processes according to the invention will be readily determinable by one of ordinary skill in the art.

The processes according to the invention can be carried out in a temperature range of from about 100° C. to about 300° C. with the preferred range being from about 150° C. to about 260° C.

The process which is highly selective for making α-olefins can be carried out in any number of ways as long as the olefin product is continuously removed. In one preferred embodiment, the process is initiated by heating an amount of a feed stream containing the carboxylic acid, the carboxylic acid anhydride, and a portion of the total amount of catalyst are heated to a temperature of from about 100° C. to about 300° C. As the olefin product forms, it is continuously removed by distillation. In another preferred embodiment, the initial reaction volume is held constant by adding additional feed in those cases where the initial volume is the same as the volume which is present during the majority of the reaction time. In yet another preferred embodiment, the process is initiated at a low initial volume, built to a larger working volume which is maintained by continuously adding additional feed stream. In another preferred embodiment, an ω-unsaturated acid is made by using a dicarboxylic acid as the carboxylic acid in the feed stream and removing the ω-unsaturated acid as quickly as it is formed. For example, 6-heptenoic acid can be made by continuously introducing a feed stream containing suberic acid at a rate sufficient to maintain the initial volume of the reaction to produce a substantially quantitative yield of 6-heptenoic acid. Additional catalyst can also be introduced at the same time either as a separate stream or in the feed stream containing the carboxylic acid and the carboxylic acid anhydride. In another embodiment, the process is initiated by heating an amount of a feed stream containing the carboxylic acid and the carboxylic acid anhydride to a temperature of from about 100° C. to about 300° C. A separate stream containing the catalyst is then introduced continuously and the olefin product is continuously removed by distillation as it forms. The process can be carried out either continuously or batch-wise as long as the olefin product is removed about as rapidly as it forms. The process can be carried out in any type of apparatus such as a batch reactor or a continuous reactor such as a plug-flow reactor, a falling-film evaporator, or an agitated thin-film evaporator (see Perry's Chemical Engineer's Handbook, 6th Ed., pages 11-33 and 11-34). A continuous process is preferred because larger amounts of α-olefin are formed in relatively shorter times, and the generation of larger, more recoverable amounts of spent catalyst which facilitates the catalyst regeneration process.

While metal recovery is enhanced by the continuous process according to the invention, both processes allow for easy catalyst recovery. This is especially important when the catalyst is a noble metal-containing catalyst such as a palladium catalyst. The spent catalyst which results from the processes according to the invention is the metal in its zero valent state. Thus reactions involving rhodium-containing catalysts produce Rh° while reactions involving palladium-containing catalysts produce Pd°. Processes employing palladium catalysts are especially economical because only low levels of catalyst are required when the catalyst is palladium-based and the dispersed palladium which is formed is easily recoverable by any means known to those of ordinary skill in the art. In a batch process, the palladium metal is simply isolated by a one time filtration. In the continuous process, the palladium metal can be recovered by any means usually employed to remove solids from continuous reaction zones such as by in-line filtration of the recirculating reaction mixture. When palladium catalyst is employed, the recovered palladium can be reconverted to the reaction catalyst by first dissolving the recovered palladium metal in aqua regia, evaporating the solution to dryness, and heating the solid residue to about 500° C. to expel HCl and $Cl_2$. The product formed is $PdCl_2$. (see R. F. Heck, Palladium Reagents in Organic Syntheses, Academic Press, N.Y., N.Y., 1985, page 18). A catalyst such as dichlorobis(triphenylphosphine)palladium(II) can be prepared from the $PdCl_2$ by the method disclosed above.

Each of the processes according to the invention can be carried out neat or in an inert solvent. Such inert solvents include hydrocarbons having sufficiently high boiling points or silicon oil. The choice of the inert solvent will depend upon the reaction temperature and pressure and can be selected by one of ordinary skill in the art. The following examples are meant to illustrate but not limit the invention.

EXAMPLE 1

A mixture of decanoic acid (100 g, 0.580 mol), acetic anhydride (59.2 g, 0.580 mol), dichlorobis(triphenylphosphine)palladium (0.0407 g, $5.8 \times 10^{-5}$ mol), and triphenylphosphine (1.52 g, $5.9 \times 10^{-3}$ mol) was heated under a slow stream of nitrogen using an oil bath maintained at 255° C. Upon reaching a reaction temperature of ca. 130° C., the acetic acid and/or acetic anhydride distilled out of the reactor into a receiver. When the reaction temperature reached 180°-190° C. decarbonylation initiated, as evidenced by the rapid liberation of gas, and 1-nonene product was distilled from the reactor. The olefin product was removed as rapidly as possible from the reactor. As material distilled from the reactor, it was continuously replaced with an equimolar mixture of decanoic acid and acetic anhydride in a rate that maintained the initial level of the reactor contents throughout the course of the entire reaction. The decarbonylation reaction proceeded rapidly until the reaction temperature reached ca. 245° C. (ca. 40 minutes reaction time), at which point the generation of gas from the reaction had ceased. The reactor was cooled and recharged with another equal portion of Pd-catalyst, heated to 255° C., and the 1-nonene product collected as before. A total of 11 consecutive runs were carried out in this fashion (occasionally adding additional triphenylphosphine as well), using a total of 0.448 g of dichlorobis(triphenylphosphine)palladium and 2.28 g of triphenylphosphine. The combined product was washed sequentially with water, 3N sodium hydroxide, and saturated aqueous sodium chloride, and then dried over anhydrous magnesium sulfate. Distillation afforded 635 g of 1-nonene (bp 144°-145° C./760 torr), which GC analysis showed to be 97.1% of the α-olefin. TON=7885.

EXAMPLE 2

A mixture of myristic acid (90.0 g, 0.394 mol) and acetic anhydride (40.2 g, 0.394 mol) was heated under reduced pressure (150 torr) using an oil bath maintained at 255° C. A small amount of a tetrahydrofuran solution containing dichlorobis(triphenylphosphine)palladium (0.453 g, $6.45 \times 10^{-4}$ mol) and triphenylphosphine (2.97 g, 0.0113 mol) was then added to the reactor in order to initiate the decarbonylation reaction. The olefin product immediately distilled from the reaction mixture into a receiver. As material distilled from the reactor, it was continuously replaced with an equimolar mixture of myristic acid and acetic anhydride at a rate that maintained the initial level of the reactor contents throughout the course of the entire reaction. The solution of Pd-catalyst was added in a slow, continuous manner in order to keep the reaction temperature between ca. 215°-220° C. The decarbonylation reaction proceeded rapidly until the catalyst supply was exhausted, whereupon the reaction temperature gradually reached ca. 245° C. and conversion of myristic acid ceased. The combined product was washed with water and distilled to afford 940 g of 1-tridecene (bp 90° C./10 torr), which GC analysis showed to be 96.3% of the αolefin. TON=7985.

EXAMPLE 3

A mixture of oleic acid (90% pure, 70.0 g), acetic anhydride (12.6 g, 0.123 mol), chlorodicarbonylrhodium (I) dimer (0.48 g, 0.0012 mol), and dimethylphenylphosphine (0.68 g, 0.0048 mol) was stirred for a few minutes at room temperature, then the pressure of the system was reduced to 45 torr and the mixture heated using an oil bath maintained at 255° C. As product distilled from the reactor, it was continuously replaced with a mixture of oleic acid and acetic anhydride (4:3 molar mixture, respectively) in a rate that maintained the initial level of the reactor contents throughout the course of the entire reaction. The olefin product was removed as rapidly as possible from the reactor. The formation of product ceased after ca. 7 hours of reaction time. The combined distillate product was washed with water and distilled to provide 197 g of 1-heptadecadiene (bp 120° C./1 torr), which was found to be 95% of 1,8-heptadecadiene by $^1$H-NMR analysis. TON=348.

EXAMPLE 4

In a procedure similar to example 3, a mixture of adipic acid monomethyl ester (140 g, 0.874 mol), acetic anhydride (44.6 g, 0.437 mol), chlorodicarbonylrhodium (I) dimer (1.70 g, 0.00437 mol), and dimethylphenylphosphine (2.50 g, 0.0181 mol) Was heated using an oil bath maintained at 255° C. and the product collected as it distilled from the reactor. The material removed from the reactor was continuously replaced with a mixture of adipic acid monomethyl ester and acetic anhydride (4:3 molar mixture, respectively) in a rate that maintained the initial level of the reactor contents throughout the course of the entire reaction. The formation of product ceased after 6.4 hours of reaction time. The combined distillate product was washed sequentially with water, saturated aqueous sodium bicarbonate, and then water again. After drying over anhydrous magnesium sulfate, distillation provided 218 g of methyl 4-pentenoate (bp 124°-128° C./760 torr), which was found by GC analysis to be 97.9% of the α-olefin. TON=218.

EXAMPLE 5

In a procedure similar to example 3, a mixture of stearic acid (70.0 g, 0.246 mol), propionic anhydride (16.0 g, 0.123 mol), chlorodicarbonylrhodium (I) dimer (0.48 g, 0.0012 mol), and dimethylphenylphosphine (0.68 g, 0.0049 mol) was heated under reduced pressure (35–45 torr) using an oil bath maintained at 255° C. and the product collected as it distilled from the reactor. The material removed from the reactor was continuously replaced with a mixture of stearic acid and propionic anhydride (4:3 molar mixture, respectively) in a rate that maintained the initial level of the reactor contents throughout the course of the entire reaction. The formation of product ceased after ca. 8 hours of reaction time. The combined distillate product was washed with water and distilled to provide 375 g of 1-heptadecene (bp 140° C./0.6 torr) which was found by GC analysis to be 93.4% of the α-olefin. TON=657.

EXAMPLE 6

In a procedure similar to example 3, a mixture of sebacic acid (30.0 g, 0.148 mol), acetic anhydride (30.3 g, 0.296 mol), and chlorocarbonylbis-(dimethylphenylphosphine)rhodium (0.66 g, 0.0015 mol) was heated using an oil bath maintained at 255° C. and the product collected as it distilled from the reactor. The material removed from the reactor was continuously replaced with a mixture of sebacic acid and acetic anhydride (1:2 molar mixture, respectively) in a rate that maintained the initial level of the reactor contents throughout the course of the entire reaction. The formation of product ceased after ca. 7 hours of reaction time. The combined distillate product was washed with water and distilled to provide 38.4 g of 1,7-octadiene (bp 114°-121°/760 torr), which was found by GC analysis to be 92.8% of the α-ω-olefin. TON=465 based on conversion of one carboxyl group to one olefin functionality.

EXAMPLE 7

A mixture of decanoic acid (10.0 g, 0.0581 mol), acetic anhydride (5.93 g, 0.0581 mol), chlorodicarbonylrhodium (I) dimer (0.113 g, $2.9\times10^{-4}$ mol), and dimethylphenylphosphine (0.16 g, 0.0012 mol) was heated under a slow stream of nitrogen using an oil bath maintained at 255° C. As product distilled from the reactor, it was continuously replaced with an equimolar mixture of decanoic acid and acetic anhydride, which also contained 0.6 mol % of dimethylphenylphosphine (relative to the decanoic acid content of the feed), in a rate that maintained the initial level of the reactor contents throughout the course of the entire reaction. The olefin product was removed as rapidly as possible from the reactor. The formation of product ceased after ca. 90 hours of reaction time. Examination of the combined distillate product by GC (using n-decane as an internal standard) showed the presence of 433 g of 1-nonene (isolated yield of 94% based on decanoic acid employed), which was found to be 99.2% of the α-olefin. TON=5915.

EXAMPLE 8

Two separate decarbonylation reactions were carried out, with one containing decanoic acid (10.0 g, 0.0581 mol), chlorocarbonylbis(triphenylphosphine)iridium (0.45 g, $5.8\times10^{-4}$ mol), triphenylphosphine (1.52 g, 0.0058 mol), and acetic anhydride (5.92 g, 0.0580 mol), while the second reaction employed only the first three materials. The reactions were heated at 255° C. and the distillate product collected from each. The material removed from each reactor was continuously replaced with either decanoic acid or an equimolar mixture of decanoic acid and acetic anhydride, depending on the run. The formation of product from the reaction using decanoic acid alone ceased after 13.5 hours of reaction time, and GC analysis of the corresponding distillate product showed that 1-nonene had been produced with a catalyst turnover number (TON; moles of olefin product per mole of Ir catalyst) of 270 and an α-olefin selectivity of 54%. On the other hand, the product formation from the run utilizing the mixture of decanoic acid and acetic anhydride continued for 19.7 hours, and GC analysis of this distillate showed that 1-nonene had been produced with a catalyst TON of 1,280 and an αolefin selectivity of 91.5%. The data for this series of reactions appears in Table 1.

EXAMPLE 9

A mixture of decanoic acid (100 g, 0.581 mol), acetic anhydride (60 g, 0.58 mol), dichlorobis(dicyclohexylphenylphosphine)palladium, and dicyclohexylphenylphosphine (ten times the molar concentration of Pd catalyst) was heated under a slow stream of nitrogen using an oil bath maintained at 255° C. As product distilled from the reactor, it was continuously replaced with an equimolar mixture of decanoic acid and acetic anhydride in a rate that maintained the initial level of the reactor contents throughout the course of the entire reaction. The distillate products from several runs which contained varied Pd catalyst concentrations were examined by GC analysis (using n-decane as internal standard) and the turnover numbers based on nonene formation calculated. For example, use of $1\times10^{-3}$ mol % of the Pd catalyst (0.0042 g, $5.8\times10^{-6}$ mol) afforded 1-nonene with a catalyst TON of 16,200 in ca. 20 minutes of total reaction time. The data for this series of reactions appears in Table 2.

TABLE 2

| Mole % Catalyst | TON |
|---|---|
| 0.5 | 1,815 |
| $1\times10^{-2}$ | 13,400 |
| $1\times10^{-3}$ | 16,200 |
| $1\times10^{-4}$ | 8,600 |
| $1\times10^{-5}$ | 7,700 |

EXAMPLE 10

A mixture of decanoic acid (100 g, 0.581), acetic anhydride (60 g, 0.58 mol), dichlorobis(dicyclohexylphenylphosphine)palladium (0.0419 g, $5.81\times10^{-5}$ mol), and dicyclohexylphenylphosphine was heated under a slow stream of nitrogen using an oil bath maintained at 255° C. As product distilled from the reactor, it was continuously replaced with an equimolar mixture of decanoic acid and acetic anhydride in a rate that maintained the initial level of the reactor contents throughout the course of the entire reaction. The distillate products from several runs which contained varied dicyclohexylphenylphosphine concentrations were examined by GC analysis (using n-decane as internal standard) and the turnover numbers based on nonene formation calculated. For example, use of 50 equivalents of dicyclohexylphenylphosphine (0.789 g, 0.00288 mol) relative to the amount of Pd catalyst used afforded 1-nonene with a TON of 25,900. The data for this series of reactions appears in Table 3.

TABLE 3

| Excess phosphine* | TON | α-olefin selectivity |
|---|---|---|
| 0 | 3860 | 86.3 |
| 1.1 | 4520 | 90.3 |
| 5 | 9035 | 93.1 |
| 10 | 13,600 | 94.8 |
| 20 | 17,800 | 94.5 |
| 50 | 25,900 | 92.2 |

*equivalents of excess dicyclohexylphenylphosphine relative to initial amount of Pd catalyst

EXAMPLE 11

A mixture of decanoic acid (100 g, 0.581 mol), acetic anhydride, dichlorobis(triphenylphosphine)palladium (0.0407 g, $5.81\times10^{-5}$ mol), and triphenylphosphine (0.761 g, 0.00290 mol) was heated under a slow stream of nitrogen using an oil bath maintained at 255° C. As product distilled from the reactor, it was continuously replaced with a mixture of decanoic acid and acetic anhydride, identical in ratio to that of the initial charge, in a rate that maintained the initial level of the reactor contents throughout the course of the entire reaction. The distillate products from several runs which contained varied decanoic acid: acetic anhydride ratios were examined by GC analysis (using n-decane as internal standard) and the catalyst efficiency and product α-olefin selectivity calculated. For example, using of a 1:1.5 ratio of decanoic acid:acetic anhydride throughout the course of an entire reaction produced 1-nonene with a catalyst TON of 14,800 and an α-olefin selectivity of 97.4%. The data for this series of reactions appears in Table 4.

TABLE 4

| $C_9CO_2H/Ac_2O$ | TON | α-olefin selectivity |
|---|---|---|
| 1/0.5 | 7,570 | 88.8 |
| 1/0.75 | 10,200 | 93.0 |
| 1/1 | 13,730 | 96.0 |
| 1/1.5 | 14,800 | 97.4 |

EXAMPLE 12

A mixture of stearic acid (20.0 g, 0.0703 mol), acetic anhydride (7.18 g, 0.0703 mol), chlorocarbonylbis(dimethylphenylphosphine)rhodium (0.155 g, $3.52\times10^{-4}$ mol, 0.5 mol %), and eicosane (internal GC standard; 1.68 g) was heated in an oil bath maintained at 255° C. (atmospheric pressure) and the volatile materials produced were allowed to distill out of the reactor. Samples were withdrawn periodically from the reaction mixture and analyzed by GC for conversion into heptadecene and also selectivity within this product fraction for the α-olefin. As the results in Table 5 show, a relatively high degree of selectivity was maintained up to a conversion of ca. one-third of the starting material. The data in Table 5 also show that the α-olefin must be removed as quickly as it is formed in order to ensure maximum yield of α-olefin.

TABLE 5

| Reaction Time (min) | Olefin Yield (%) | α-olefin selectivity (%) |
|---|---|---|
| 5 | 22.3 | 96.4 |
| 10 | 33.5 | 93.7 |
| 20 | 54.7 | 85.7 |
| 40 | 57.7 | 74.8 |
| 60 | 56.4 | 67.7 |

EXAMPLE 13

In a procedure similar to example 3, a mixture of suberic acid (20.0 g, 0.115 mol), acetic anhydride (11.7 g, 0.115 mol), and chlorocarbonyl bis(dimethylphenylphospine)rhodium (0.509 g, 0.00115 mol) was heated under reduced pressure (100 torr) using an oil bath maintained at 255° C. and the product collected as it distilled from the reactor. The material removed was continuously replaced with a mixture of suberic acid and acetic anhydride (1:1 molar mixture; a total of 90.0 g of suberic acid was used in the feed mixture) in a rate that maintained the initial level of the reactor contents throughout the course of the entire reaction. The formation of product ceased after about 90 minutes of reaction time. The distillate product collected was fractionally distilled to provide 54.1 g of 6-heptenoic acid (bp 95°–100° C./10 torr) which was found by GC analysis to be >98% of the α-olefin. This amount of product corresponds to a catalyst TON of 368. Considering the amount of unreacted suberic acid containing residue recovered in the distillation pot (19.6 g), the isolated yield of 6-heptenoic acid relative to the suberic acid in the feed mixture was nearly quantitative.

EXAMPLE 14

A mixture of stearic acid (150 g, 0.527 mol), acetic anhydride (54 g, 0.53 mol), and triphenylphosphine (0.921 g, $3.51\times10^{-3}$ mol) was heated to 220°–230° C. under reduced pressure (55 torr) in a 500 mL flask fitted with a distillation head for product removal. Into this solution was pumped a feed mixture composed of stearic acid (400 g, 1.41 mol), acetic anhydride (150 g, 1.47 mol), dichlorobis(triphenylphosphine)palladium (0.0492 g, 7.03×10$^{-5}$ mol), and triphenylphosphine (0.921 g, 3.51×10$^{-3}$ mol) This feed mixture was maintained at ca. 90° C. and introduced into the reactor via a stainless steel tube with the opening positioned below the solution level. As product distilled from the reactor it was continuously replaced with more feed mixture at a rate of introduction that was approximately equal to the rate of product removal in order to maintain a constant level of the reaction mixture. The reaction was continued in this manner until the supply of feed mixture was exhausted (ca. 3.5 hours). At the conclusion of the reaction the level of reactor contents was about the same as at the beginning of the reaction. The distillate product was fractionally distilled to afford 237 g of 1-heptadecene (bp 130°-135° C./0.4 torr) which was found by GC analysis to be 95.6% of the α-olefin. This amount of product corresponds to a catalyst TON of 13,515. Considering the amount of unreacted stearic acid-containing residue recovered in the distillation pot (94 g), the isolated yield of 1-heptadecene relative to the stearic acid in the feed mixture was at least 92%.

Typical GC conditions for analyses conducted for Examples 1-14 are the following: Supelco SPB-5 fused silica capillary column; 30 m, 0.25 mm ID, 0.25 mm film thickness; 60° C. for 2 min., increasing in temperature at 25° C. per minute up to 280° C.

What is claimed is:

1. A process for making olefins in high yield comprising maintaining a reaction mixture comprised of a carboxylic acid wherein said carboxylic acid has at least three carbon atoms and at least one β-hydrogen atom, a carboxylic acid anhydride, and a Group VIII metal-containing catalyst or a copper-containing catalyst at a temperature of from about 100° C. to about 300° C.

2. The process of claim 1 wherein said Group VIII metal-containing catalyst is a palladium, rhodium, or iridium catalyst.

3. The process of claim 1 wherein said reaction mixture is further comprised of a ligand having a trivalent donor atom.

4. The process of claim 3 wherein said ligand is phosphine or a phosphine derivative.

5. The process of claim 4 wherein the molar phosphorus/Group VIII metal ratio is from about 1/1 to about 1000/1.

6. The process of claim 5 wherein said molar phosphorus/Group VIII metal ratio is from about 2/1 to about 100/1.

7. The process of claim 2 wherein said palladium catalyst is dichlorobis(triphenylphosphine)palladium.

8. The process of claim 2 wherein said palladium catalyst is dichlorobis(dicyclohexylphenylphosphine)palladium.

9. The process of claim 2 wherein said rhodium catalyst is chloro(carbonyl)bis(dimethylphenylphosphine)rhodium.

10. The process of claim 2 wherein said Group VIII metal-containing catalyst or said copper-containing catalyst is employed in an amount from about 10$^{-6}$ mole % to about 10.0 mole % based on the number of moles of carboxylic acid introduced into the reactor.

11. The process of claim 2 wherein when the metal in said Group VIII metal-containing catalyst is rhodium, said catalyst is employed in an amount from about 0.1 mole % to about 1.0 mole % based on the number of moles of carboxylic acid introduced into the reactor.

12. The process of claim 2 wherein when the metal in said Group VIII metal-containing catalyst is palladium, said catalyst is employed in an amount from about 10$^{-2}$ mole % to about 10$^{-3}$ mole % based on the number of moles of carboxylic acid introduced into the reactor.

13. The process of claim 1 wherein said process is carried out at a total pressure greater than 1.0 atmosphere.

14. The process of claim 1 wherein said process is carried out at a total pressure less than 1.0 atmosphere.

15. The process of claim 1 wherein said temperature is from about 150° C. to about 260° C.

16. The process of claim 1 wherein said carboxylic acid has from about 8 to about 22 carbon atoms.

17. The process of claim 16 wherein said carboxylic acid is stearic acid.

18. The process of claim 16 wherein said carboxylic acid is decanoic acid.

19. The process of claim 16 wherein said carboxylic acid is myristic acid.

20. The process of claim 16 wherein said carboxylic acid is oleic acid.

21. The process of claim 16 wherein said carboxylic acid is palmitic acid.

22. The process of claim 16 wherein said carboxylic acid is lauric acid.

23. The process of claim 1 wherein said carboxylic acid is a dicarboxylic acid having from 4 to about 20 carbon atoms between the carboxyl groups.

24. The process of claim 17 wherein said dicarboxylic acid is sebacic acid.

25. The process of claim 17 wherein said dicarboxylic acid is suberic acid.

26. The process of claim 17 wherein said dicarboxylic acid is azelaic acid.

27. The process of claim 17 wherein said dicarboxylic acid is adipic acid.

28. The process of claim 1 wherein said carboxylic acid anhydride is acetic anhydride or propionic anhydride.

29. The process of claim 28 wherein said anhydride is acetic anhydride.

30. A process which is highly selective for making α-olefins in high yield comprising maintaining a reaction mixture comprised of a carboxylic acid wherein said carboxylic acid has at least three carbon atoms and at least one β-hydrogen atom, a carboxylic acid anhydride with a Group VIII metal-containing catalyst or a copper-containing catalyst at a temperature of from about 100° C. to about 300° C. to form an olefin product comprised of at least 90% by weight of an α-olefin while continuously removing said olefin product from said reaction mixture.

31. The process of claim 30 wherein said Group VIII metal-containing catalyst is a palladium, rhodium, or iridium catalyst.

32. The process of claim 30 wherein said reaction mixture is further comprised of a ligand having a trivalent donor atom.

33. The process of claim 30 wherein said ligand is phosphine or a phosphine derivative.

34. The process of claim 33 wherein the molar phosphorus/Group VIII metal ratio is from about 1/1 to about 1000/1.

35. The process of claim 33 wherein said molar phosphorus/Group VIII metal ratio is from about 2/1 to about 100/1.

36. The process of claim 31 wherein said palladium catalyst is dichlorobis(triphenylphosphine)palladium.

37. The process of claim 31 wherein said palladium catalyst is dichlorobis(dicyclohexylphenylphosphine)palladium.

38. The process of claim 31 wherein said rhodium catalyst is chloro(carbonyl)bis(dimethylphenylphosphine)rhodium.

39. The process of claim 30 wherein said Group VIII metal-containing catalyst or said copper-containing catalyst is employed in an amount from about $10^{-6}$ mole % to about 10.0 mole % based on the number of moles of carboxylic acid introduced into the reactor.

40. The process of claim 30 wherein when the metal in said Group VIII metal-containing catalyst is rhodium, said catalyst is employed in an amount from about 0.1 mole % to about 1.0 mole % based on the number of moles of carboxylic acid introduced into the reactor.

41. The process of claim 30 wherein when the metal in said Group VIII metal-containing catalyst is palladium, said catalyst is employed in an amount from about $10^{-2}$ mole % to about $10^{-3}$ mole % based on the number of moles of carboxylic acid introduced into the reactor.

42. The process of claim 30 wherein said process is carried out at a total pressure greater than 1.0 atmosphere.

43. The process of claim 30 wherein said process is carried out at a total pressure less than 1.0 atmosphere.

44. The process of claim 30 wherein said temperature is from about 150° C. to about 260° C.

45. The process of claim 30 wherein said carboxylic acid has from about 8 to about 22 carbon atoms.

46. The process of claim 45 wherein said carboxylic acid is stearic acid.

47. The process of claim 45 wherein said carboxylic acid is decanoic acid.

48. The process of claim 45 wherein said carboxylic acid is myristic acid.

49. The process of claim 45 wherein said carboxylic acid is oleic acid.

50. The process of claim 45 wherein said carboxylic acid is palmitic acid.

51. The process of claim 45 wherein said carboxylic acid is lauric acid.

52. The process of claim 30 wherein said carboxylic acid is a dicarboxylic acid having from 4 to about 20 carbon atoms between the carboxyl groups.

53. The process of claim 52 wherein said dicarboxylic acid is sebacic acid.

54. The process of claim 52 wherein said dicarboxylic acid is suberic acid.

55. The process of claim 52 wherein said dicarboxylic acid is azelaic acid.

56. The process of claim 52 wherein said dicarboxylic acid is adipic acid.

57. The process of claim 30 wherein said reaction mixture is generated by continuously adding said catalyst to said carboxylic acid and said carboxylic acid anhydride.

58. The process of claim 30 wherein additional amounts of said carboxylic acid and said carboxylic acid anhydride are continuously added to said reaction mixture.

59. The process of claim 56 wherein said additional amounts of said carboxylic acid and said carboxylic acid anhydride are continuously added to said reaction mixture at a rate sufficient to maintain the initial volume of said reaction mixture.

60. The process of claim 30 wherein additional amounts of said carboxylic acid, said carboxylic acid anhydride, and said catalyst are continuously added to said reaction mixture.

61. The process of claim 30 wherein said olefin product contains at least 95% by weight α-olefin.

62. The process of claim 30 wherein said carboxylic acid anhydride is acetic anhydride or propionic anhydride.

63. The process of claim 62 wherein said anhydride is acetic anhydride.

* * * * *